(12) United States Patent
Ogle et al.

(10) Patent No.: US 6,468,660 B2
(45) Date of Patent: Oct. 22, 2002

(54) BIOCOMPATIBLE ADHESIVES

(75) Inventors: Matthew F. Ogle, Oronoco, MN (US); Andrea L. McConico, Fridley, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 18 days.

(21) Appl. No.: 09/751,963

(22) Filed: Dec. 29, 2000

(65) Prior Publication Data

US 2002/0122944 A1 Sep. 5, 2002

(51) Int. Cl.[7] ............................................. B32B 27/36

(52) U.S. Cl. ..................... 428/413; 524/9; 524/10; 524/14; 524/21; 623/2.1

(58) Field of Search ................ 428/413; 524/9, 524/10, 14, 21; 623/2.1; 11/11

(56) References Cited

U.S. PATENT DOCUMENTS

| | | | |
|---|---|---|---|
| 3,278,561 A | | 10/1966 | Gaertner |
| 3,678,131 A | * | 7/1972 | Klapprott et al. ........ 260/837 R |
| 4,268,656 A | * | 5/1981 | Ray-Chaudhuri et al. ... 528/103 |
| 4,414,976 A | | 11/1983 | Schwarz et al. |
| 4,626,310 A | | 12/1986 | Ritter |
| 4,650,678 A | | 3/1987 | Fuhge et al. |
| 4,740,534 A | | 4/1988 | Matsuda et al. |
| 4,798,885 A | * | 1/1989 | Mason et al. ................ 530/350 |
| 4,818,291 A | | 4/1989 | Iwatsuki et al. |
| 4,841,962 A | * | 6/1989 | Berg et al. ................... 128/156 |
| 4,983,392 A | | 1/1991 | Robinson |
| 4,985,516 A | | 1/1991 | Sakashita et al. |
| 4,994,542 A | | 2/1991 | Matsuda et al. |
| 5,160,790 A | | 11/1992 | Elton |
| 5,173,301 A | | 12/1992 | Itoh et al. |
| 5,218,073 A | | 6/1993 | Evans |
| 5,266,608 A | | 11/1993 | Katz et al. |
| 5,280,069 A | | 1/1994 | Dobinson et al. |
| 5,292,333 A | | 3/1994 | Johnson |
| 5,385,606 A | | 1/1995 | Kowanko |
| 5,486,547 A | | 1/1996 | Matsuda et al. |
| 5,512,527 A | | 4/1996 | Ritter |
| 5,583,114 A | | 12/1996 | Barrows et al. |
| 5,591,820 A | | 1/1997 | Kydonieus et al. |
| 5,653,730 A | | 8/1997 | Hammerslag |
| 5,855,620 A | | 1/1999 | Bishopric et al. |
| 6,379,379 B1 | * | 4/2002 | Wang ........................ 623/1.15 |
| 6,379,615 B1 | * | 4/2002 | Ogle ............................ 422/28 |
| 6,391,538 B1 | * | 5/2002 | Vyavahare et al. .......... 435/1.1 |

FOREIGN PATENT DOCUMENTS

| | | |
|---|---|---|
| DE | 198 49 589 C 1 | 6/2000 |
| EP | 0 199 247 A2 | 10/1986 |
| EP | 0 332 405 A2 | 9/1989 |
| EP | 0 747 066 A2 | 12/1996 |
| WO | WO 92/09301 | 6/1992 |
| WO | WO 92/09309 | 6/1992 |
| WO | WO 94/01508 | 1/1994 |
| WO | WO 97/32615 | 9/1997 |
| WO | WO 98/59011 | 12/1998 |

OTHER PUBLICATIONS

M.J. MacPhee, "Commercial Pooled–Source Fibrin Sealant", Surgical Adhesive and Sealants, Edited by David Sierra and Renato Saltz, pp. 13–18.

(List continued on next page.)

*Primary Examiner*—Robert Dawson
*Assistant Examiner*—Christopher M. Keehan
(74) *Attorney, Agent, or Firm*—Hallie A. Finucane; Patterson, Thuente, Skaar & Christensen, P.A.; Peter S. Dardi

(57) ABSTRACT

Novel adhesive compositions are described that include an epoxyamine and, preferably, a curing agent. The adhesive composition can be used in surgical settings such as implanting bioprostheses and/or in manufacturing of bioprostheses. Biocompatible substrates can be adhered together by an adhesive bond formed by curing of the epoxyamine adhesive composition.

29 Claims, 4 Drawing Sheets

OTHER PUBLICATIONS

Young et al., "Fibrin Suture of Peripheral Nerves", The Lancet, Aug. 3, 1940, pp. 126–128.

Young et al., "Nerve Regeneration", The Lancet, Aug. 3, 1940, pp. 128–132.

Ross et al., "Some Reactions of Epichlorohydrin with Amines", The Journal of Organic Chemistry, vol. 29, Jan.–Apr. 1964, pp. 824–826.

G. Köveker, "Clinic Application of Fibrin Glue in Cardiovascular Surgery", Thorac. Cardiovasc. Surgeon 30, 1982, pp. 228–229.

Brands et al., "Treatment of Ruptured Kidney by Gluing with Highly Concentrated Human Fibrinogen", Journal of Pediatric Surgery, vol. 18, No. 5, Oct. 1983, pp. 611–613.

Meyers et al., "A Fibrin Adhesive Seal for the Repair of Osteochondral Fracture Fragments", Clinical Orthopaedics and Related Research, No. 182, Jan.–Feb. 1984, pp. 258–263.

Sugiura et al., "A New Method for Venous Interposition Grafts Using Fibrin Glue", Microsurgery vol. 6, 1985, pp. 125–128.

Hasegawa et al., "Closure of Carotid–Cavernous Fistulae by Use of a Fibrin Adhesive System", Surg. Neurol., 1985, vol. 24, pp. 23–26.

Keller et al., "Fixation of Osteochondral Fractures", Acta. Orthop. Scand., vol. 56, 1985, pp. 323–326.

Kram et al., "Tracheal Repair with Fibrin Glue", J. Thorac. Cardiovasc. Surg., 1985, vol. 90, pp. 771–775.

Bornemisza et al., "Restoration of Skin Defects with Fibrin Glue", Acta Chirurgica Hungarica, vol. 27(4), 1986, p. 249–258.

Chezlov et al., "Production of N,N,N–Triglycidylamine", USSR, Zh.Prikl. Khim. (Leningrad), 1990, 63(8), pp. 1877–1878, Coden: ZPKHAB; ISSN: 0044–4618, Journal written in Russian. CAN 114:121880.

Seymour S. Block, "Disinfection, Sterilization and Preservation", Lea & Febiger, 1991, pp. 1050–1051 & 1060.

Chezlov et al., "Structure and Reactivity of Oxirane–Type Chemical Modifiers for Gelatin", St. Petersburg, Russia, Zh. Prik Khim (St. Petersburg), 1998, vol. 71(1), pp. 149–156, Coden: ZPKHAB; ISSN: 0044–4618, Journal written in Russian. CAN 129:17075.

International Search Report (PCT/US01/49336) dated Aug. 5, 2002.

* cited by examiner

BIOCOMPATIBLE ADHESIVES

BACKGROUND OF THE INVENTION

The invention relates to compositions suitable for use as adhesives, especially for medical products. This invention also relates to medical devices that include portions bonded together by the adhesives.

Adhesives can be used in the medical field in a variety of ways. Medical adhesives can be used, for example, in manufacturing and/or implantation of medical devices. In surgical settings, medical adhesives provide an alternative to sutures, staples and the like for closing wounds in soft tissue. Certain tissues, such as nerves and particular vital organs, are too delicate for suturing or stapling, so the use of medical adhesives may be a viable repair option. In manufacturing settings, medical adhesives can be used to adhere one or more components of a medical device together.

Generally, the use of an adhesive for the manufacturing and/or implantation of medical devices or to repair wounds in soft tissue can be desirable due to potential sealing properties and uniform stress distribution. Adhesives provide a means for attaching substrates in the medical devices. The use of an adhesive may form an adhesive bond over the length of an attachment site. Adhesives tend to distribute the stress exerted on the attachment site over the length of the attachment site.

Generally, medical adhesives can be classified according to whether they include synthetic polymers, natural (biological) polymers or both. A variety of synthetic urethane based polymers have been developed as medical glues. Natural surgical adhesives generally are based on proteins. For example, fibrin glues include the protein fibrinogen. Fibrinogen is used in natural wound healing mechanisms in humans and other mammals. Synthetic adhesives have the disadvantage of being potentially toxic. On the other hand, biological/natural adhesives generally have relatively low binding (cohesive) strengths and rapid degradation times.

SUMMARY OF THE INVENTION

In a first aspect, the invention pertains to an adhesive composition including an epoxyamine and a curing agent. The epoxyamine is at a concentration of between about 25 percent by weight and about 90 percent by weight in the adhesive composition.

In a further aspect, the invention pertains to a prosthesis including a first substrate. The first substrate is associated with an adhesive composition that includes an epoxyamine. The concentration of the epoxyamine in the adhesive composition is between about 25percent by weight and about 90 percent by weight.

In another aspect, the invention pertains to method of securing a first substrate to a second substrate. The method includes contacting a first substrate including an adhesive composition with a second substrate to form an adhesive bond between the first and the second substrate. The adhesive composition includes an epoxyamine.

In a further aspect, the invention pertains to a method of manufacturing a heart valve prosthesis. The method includes associating a first valve component with an adhesive composition and adhering the first valve component with a second valve component to form an adhesive bond between the first valve component and the second valve component. The adhesive composition includes an epoxyamine.

In another aspect, the invention pertains to a prosthesis including at least two substrates. The substrates are adhered together by an adhesive bond. The adhesive bond is formed when an epoxyamine adhesive between the substrates is cured.

DETAILED DESCRIPTION OF THE PREFERRED EMBODIMENTS

Figure 1:
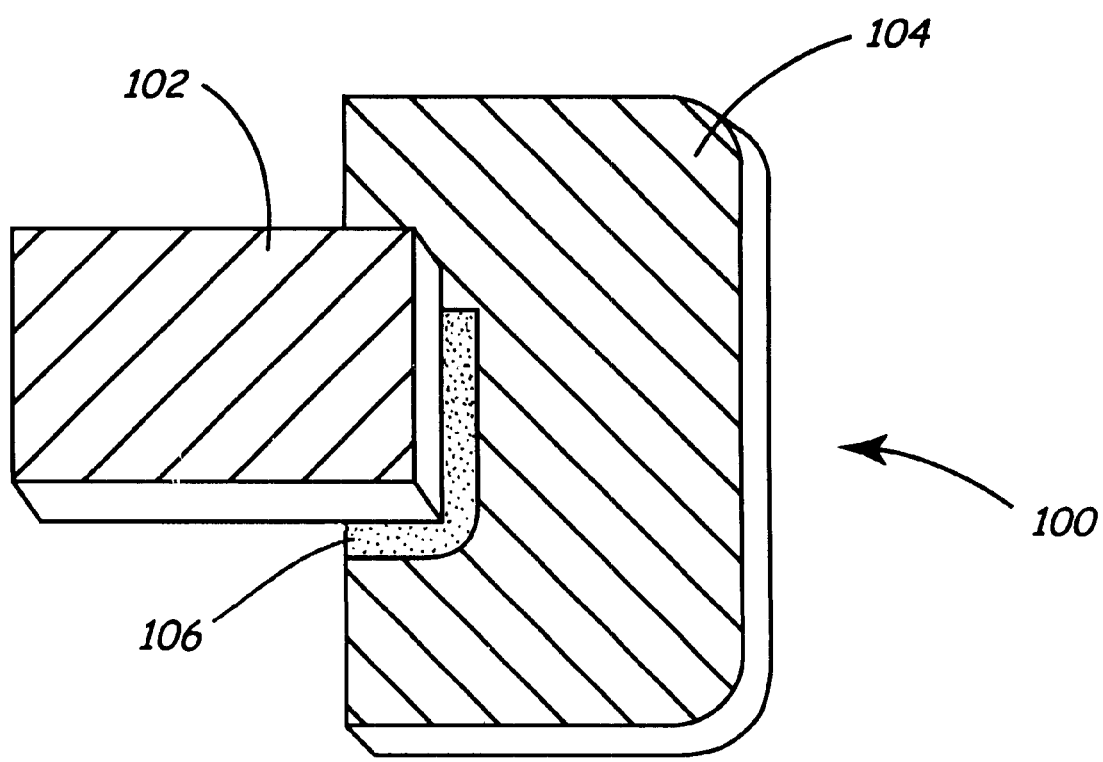
FIG. 1 is a schematic perspective view of a first substrate joined to a second substrate with a medical adhesive.

Novel medical adhesive compositions have been developed that include epoxyamines. The adhesive compositions are useful for producing medical devices and in surgical procedures. The adhesive composition can be particularly useful for adhesion of tissue to tissue and for adhesion of tissue to other materials. The adhesive composition may, optionally, include curing agents that accelerate the curing process and/or flexibilizers.

In particular, the adhesive composition is associated with a first biocompatible substrate. The biocompatible substrate associated with an epoxyamine adhesive can be joined to a second biocompatible substrate. An adhesive bond can form between the first and the second substrate upon curing of the adhesive. The adhered first and second substrates can be incorporated, for example, into a medical device. In alternative embodiments, a biocompatible substrate can be associated with the adhesive and adhered to native tissue in a patient. The adhesive may also be used in wound healing to adhere two sections of native tissue together.

A substrate with the associated adhesive can form all or part of a medical device. The adhesives are useful for the attachment of two biocompatible substrates to each other prior to and/or during implantation of the substrates into the patient. The use of the adhesives can be part of a manufacturing process of a prosthesis in which two or more substrates are incorporated into the prosthesis. The adhesive may also be used as a substitute for sutures and/or staples in the assembly of a prosthesis, in attaching the prosthesis to native tissue and/or in repairing native tissue.

The use of an adhesive can be less damaging to substrates than, for example, sutures and staples. The use of the adhesives described herein in producing medical devices is desirable due to the low toxicity of the cured epoxyamine adhesive. In addition, the use of the adhesive is desirable due to potential sealing properties and uniform stress distribution.

The adhesive compositions include one or more epoxyamines. The epoxyamine can bond with a number of functional groups that may potentially be present on the biocompatible substrates, particularly tissue. Biocompatible substrates can include tissue, and/or synthetic materials that include, for example, polymers with the appropriate functional groups to bind to the epoxyamines.

The epoxyamine in the adhesive has unreacted epoxy groups that can react to form chemical bonds with a variety of functional groups including, for example, thiols, alcohols, amines and the like. The substrates may include inherently or e modified to include the functional groups that are reactive with the epoxyamine. Chemical bonding as referred to herein refers to all types of chemical bonding, including covalent bonding. In preferred embodiments, the epoxyamine in the adhesive forms covalent bonds with the substrates.

A curing agent that includes, for example, thiol, alcohol, and/or amine functional groups may be included in the adhesive. Preferred curing agents are multifunctional molecules. Generally, a curing agent can assist in formation of a strong adhesive bond by facilitating crosslinking throughout the material. The curing agent can accelerate the curing process of the adhesive by reacting with the epoxyamine. Preferably, the curing agent forms covalent bonds with the epoxyamine. curing agents generally do not react with the substrate.

Referring to FIG. 1, the overall arrangement of the resulting structure 100 has a first substrate 102 bound to a second substrate 104 with a medical adhesive 106 between substrate 102 and substrate 104. Substrate 102 or a portion of substrate 102 forms a seal or adhesive bond with the substrate 104 or a portion of the substrate 104.

Methods described herein include contacting a first substrate, associated with an adhesive, to a second substrate. An adhesive bond can be formed between the first substrate and the second substrate upon curing of the adhesive. In some embodiments, some of the adhesive components may be resorbed over time and any potential alterations of the mechanical properties of the tissue caused by the resorption of the adhesive are believed to be replaced by mechanical properties of healed natural tissue.

In other embodiments, the medical adhesive can be used to attach a prosthesis to the native support tissue within a patient. Preferably, a portion or all of the prosthesis and/or the patients' support tissue is associated with the epoxyamine adhesive. After application of the adhesive to the prosthesis and/or the support tissue, the prosthesis is attached to the support tissue. For. example, a cardiac prosthesis, such as a heart. valve prosthesis or an annuloplasty ring, can be secured to the corresponding native support tissue (i.e., annulus) within the patient using the medical adhesive of the invention. In alternative embodiments, the adhesive can be associated with native tissue to promote wound healing.

The adhesive described herein can be used in the manufacturing of prostheses, particularly heart valve prostheses. Two or more. substrates can be contacted with each other with the adhesive between all or portions of the substrates. An adhesive bond then forms between the substrates upon curing of the adhesive.

The adhesives can also be used for the formation of prostheses such as surgical patches. The patch can include multiple layers. The multiple layers of the patch can be applied sequentially to the wound, or they can be adhered either completely or partially to each other with the adhesive prior to application to the wound. Generally, the top layer of the patch may be the same size or larger than the underlying layers. The medical adhesive can be used to fasten the layers together and/or to bind the patch to the wound site. The layers can be formed from tissue, such as pericardial tissue, or a synthetic material.

The adhesive preferably forms an interface between the first substrate and second substrate with suitable porosity and hydrophilicity. In particular, the adhesive interface should be sufficiently porous such that the adhesive can incorporate into or with the biocompatible material to achieve mechanical interlocking between the two substrates and the adhesive. Similarly, an adhesive interface between a tissue and a biocompatible substrate should be sufficiently hydrophilic such that the adhesive will wet the substrate, allowing complete contact between substrates and adhesive to form a secure bond.

To form an adhesive bond between any two substrates, a first substrate associated with the adhesive is generally contacted with a second substrate. Preferably, the adhesive is generally applied shortly before forming the seal or adhesive bond between the first substrate and the second substrate. Then, the adhesive bond is formed, and the adhesive bond is held together while the medical adhesive cures sufficiently to secure the adhesive bond.

A. Prostheses and Patches

Relevant prostheses can include a tissue substrate and/or non-tissue substrate. The substrate is suitable for attachment or association using the improved adhesive. Generally, the prostheses are designed for implantation into or onto a patient for extended periods of time. Prostheses include, for example, prosthetic hearts, prosthetic heart valves, annuloplasty rings, vascular and coronary and structural stents, vascular grafts or conduits, anastomotic connectors, leads, pacing leads, guidewires, permanently in-dwelling percutaneous devices, vascular or cardiovascular shunts, dermal grafts for wound healing, surgical patches, neurological growth supports, Hickman catheters, and bone replacement grafts, such as joint replacement prostheses.

Prostheses of particular interest include implantable vascular devices. "Vascular" devices and structures as used herein include cardiovascular devices and structures and other blood contacting devices and structures. Implantable vascular devices include, for example, vascular grafts and conduits, pacemakers, valved grafts, stents, heart valves, patches, and anastomotic connectors.

B. Substrates

Appropriate biocompatible substrates for attachment with the improved adhesives described herein can include tissue and other natural and/or synthetic materials. The substrate can be native tissue in a patient and/or can be formed from natural materials, synthetic materials or combinations thereof. Natural, i.e., biological, material for use in the invention includes relatively intact living tissue, decellularized tissue and recellularized tissue. These tissues may be obtained from, for example, natural heart valves, portions of natural heart valves such as aortic roots, walls and leaflets, pericardial tissues, such as pericardial patches, connective tissues, bypass grafts, tendons, ligaments, skin patches, blood vessels, cartilage, dura mater, skin, bone, fascia, submucosa, umbilical tissues, and the like.

Natural tissues are derived from a selected animal species, typically mammalian, such as human, bovine, porcine, seal, equine, or kangaroo. These natural tissues generally include collagen-containing material. Natural tissue is typically, but not necessarily, soft tissue. Tissue materials are particularly useful for the formation of tissue heart valve prostheses. The tissue can be living tissue, decellularized tissue or recellularized tissue. Decellularization approaches are described, for example, in U.S. Pat. No. 5,855,620, incorporated herein by reference.

Tissues can be fixed by crosslinking. Fixation provides mechanical stabilization, for example, by preventing enzymatic degradation of the tissue. Glutaraldehyde or formaldehyde is typically used for fixation, but other fixatives can be used, such as other difunctional aldehydes, epoxides, and genipin and derivatives thereof. Tissues can be used in either crosslinked or uncrosslinked form, depending on the type of tissue, the use and other factors. Generally, if xenograft tissue is used, the tissue is crosslinked and/or decellularized.

Relevant synthetic materials for association with the adhesive include, for example, polymers and ceramics. Appropriate ceramics include, without limitation, hydroxyapatite, alumina and pyrolytic carbon. Ceramics can be coated with a polymer, protein or other compound prior to use as a substrate, if desired. Appropriate synthetic materials can include hydrogels and other synthetic materials that cannot withstand severe dehydration.

Substrate materials can be fabricated from synthetic polymers as well as purified biological polymers. Appropriate synthetic polymers include, without limitation, polyamides (e.g., nylon), polyesters, polystyrenes, polyacrylates, vinyl polymers (e.g., polyethylene, polytetrafluoroethylene, polypropylene and polyvinyl chloride), polycarbonates, polyurethanes, poly dimethyl siloxanes, cellulose acetates, polymethyl methacrylates, ethylene vinyl acetates, polysulfones, nitrocelluloses and similar copolymers. These synthetic polymeric materials can be woven or knitted into a mesh or fabric to form a matrix or substrate. Alternatively, the synthetic polymer materials can be molded or cast into appropriate forms.

Biological polymers can be naturally occurring or produced in vitro by fermentation and the like. Purified biological polymers can be appropriately formed into a substrate by techniques such as weaving, knitting, casting, molding, extrusion, cellular alignment and magnetic alignment. Suitable biological polymers include, without limitation, collagen, elastin, silk, keratin, gelatin, polyamino acids, polysaccharides (e.g., cellulose and starch) and copolymers thereof.

Non-tissue substrates may also include metals. Suitable metals include, for example, titanium, stainless steel, cobalt, and alloys such as Elgiloy®, a cobalt-chromium-nickel alloy and Nitinol, a nickel-titanium alloy.

The particular substrate for association with an adhesive can form the entire medical device or it can form portions of the medical device. Similarly, different substrates can be combined to form the medical device. For example, a fixed, xenograft tissue heart valve can be combined with a fabric sewing cuff to form a heart valve prosthesis. The fixed tissue and/or the sewing cuff can be associated with the adhesive. The adhesive can be associated with the substrate before or after the various portions are combined into the medical device. The selected approaches for association of the adhesive with the substrate or substrates may influence the order of construction of the medical device.

Prostheses may also include components that are not suitable for association with the adhesive. These components may be incorporated into the prostheses by sutures, staples and the like. The prostheses, however, can include one or more substrates that can be associated with the adhesive to form an adhesive bond with another substrate.

C. Adhesive

Suitable adhesives include an epoxyamine composition and may include additional components. Other adhesive components may include curing agents, flexibilizers and various additives described in more detail below.

In preferred embodiments, one or more epoxyamine compounds are used in the adhesive. Epoxyamines are molecules that generally include both an amine moiety (e.g. a primary, secondary, tertiary, or quaternary amine) and an epoxide moiety. The epoxyamine compound can be a monoepoxyamine compound and/or a polyepoxyamine compound. The epoxyamine compound is preferably a polyepoxyamine compound having at least two epoxide moieties and possibly three or more epoxide moieties. In some preferred embodiments, the polyepoxyamine compound is triglycidylamine (TGA) as shown in FIG. 2.

In epoxyamines, the epoxide ring is preferably separated from the nearest amino moiety by between 1 and 5 atoms, i.e., a $C_1$–$C_5$ branched or linear alkyl or substituted alkyl chain, such as the methylene group, which separates the epoxide ring and the tertiary amine moiety in TGA. Other chemical groups which can be interposed between the epoxide ring and the nearest amino moiety include, for example, branched or linear alkenyl chains, substituted alkyl chains, ring groups and aromatic groups.

Polyepoxyamine compounds can be synthesized using methods known in the art. These methods include, for example, approaches described by Ross et al., 1963 J. Org. Chem. 29:824–826, Martyanova et al., 1990, Sb. Nauch. Tr. Lenengr. In-t Kinoinzh. 2:139–141 (Chem. Abst. Nos. 116:43416 and 116:31137) and Chezlov et al., 1990, Zh. Prikl. Khim. (Leningrad) 63:1877–1878 (Chem. Abst. No. 114:121880), all of which are incorporated herein by reference.

Figure 2:
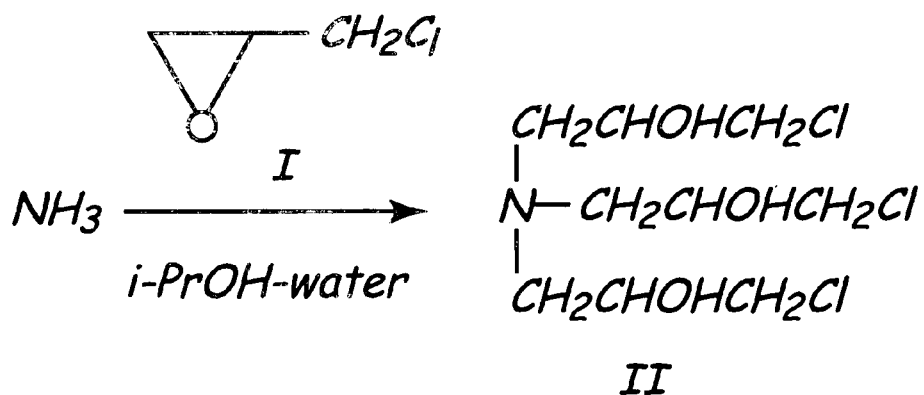
FIG. 2 is a schematic diagram of a reaction for preparing triglycidylamine (TGA).
Figure 2:
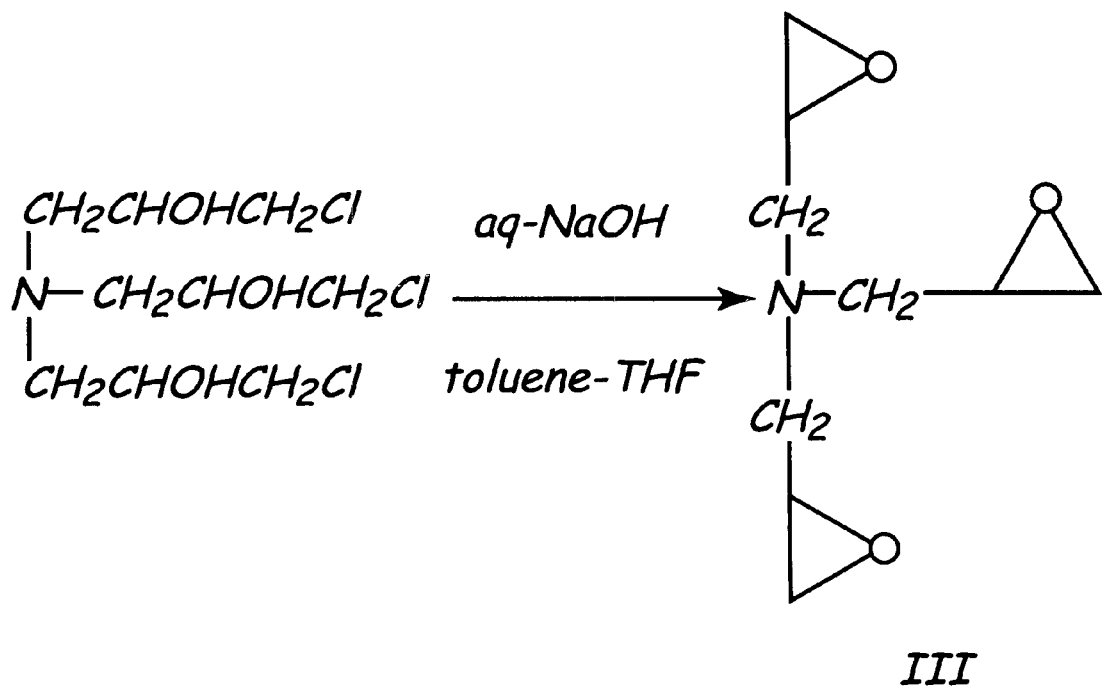

One method of synthesizing TGA is depicted in FIG. 2. Briefly, epichlorohydrin (compound I in FIG. 2) is reacted with ammonia (roughly 1:5 molar ratio with epichlorohydrin) in isopropanol with ammonium triflate as a catalyst. The reaction proceeds for about 48 hours. Following removal of volatile components, the mixture yields a viscous syrup. The syrup, after removal of unreacted epichlorhydrin with water and drying, can be dissolved in toluene and concentrated under reduced pressure to yield tris-(3-chloro-2-hydroxypropyl) amine (compound II in FIG. 2).

Compound II can be dissolved in toluene, followed by addition of tetrahydrofuran, sodium hydroxide and water. The mixture is stirred for several hours with a powerful stirrer and cooled with ice water. Then, the organic layer can be separated from the aqueous layer. The aqueous layer can be extracted with toluene and the organic phases combined. The combined organic phases are dried overnight with a dessicant. After removing the dessicant, the solution can be concentrated under reduced pressure and the residue vacuum distilled to yield TGA (Compound III in FIG. 2). TGA can be recovered as a viscous liquid, having a boiling point of 98° C.–101° C. Liquid TGA can solidify upon refrigeration and remain a solid when returned to room temperature. The concentration of the TGA in the liquid is generally at least about 95 percent by weight or more and preferably greater than about 99 percent by weight.

Epoxyamines can self-polymerize, if left for a period of time, to form epoxyamine polymers. Self-polymerization occurs when epoxy moieties react with the primary, secondary or tertiary amines. Polymerization of a polyepoxyamine compound may lead to formation of a polymer having a plurality of quaternary ammonium moieties. Adhesives, thus, can include monomers of the polyepoxyamine compound and/or a distribution of oligomers of the polyepoxyamine compound due to the self-polymerization.

In some embodiments, only one epoxyamine compound is used in the adhesive. In other embodiments, a plurality of different epoxyamine compounds are used in the adhesive, such as a combination of TGA and a quaternary form of epoxyamine.

The epoxyamine compounds can have high reactivity with a variety of functional groups including, for example, alcohols, amines, sulfur containing functional groups, such as thiols and the like. The epoxyamines can react, for example, with functional groups in proteins, for example, when the substrate is tissue. The epoxyamines can also react with functional groups present on other suitable substrates, e.g. a synthetic polymer with appropriate functional groups.

For example, polyurethanes can be synthesized with essentially any desirable functional group, such as thiols. In other examples, polyvinyl alcohol has OH functional groups, and polyacrylamide has functional groups that can bond covalently.

The epoxyamine is generally diluted with a solvent to obtain the desired concentration of epoxyamine in the adhesive. The concentration can be selected to yield desired viscosity and cure times. Preferably, the solvent is aqueous. The concentration of the epoxyamine in the adhesive can be between about 25 percent by weight and about 90 percent by weight. Preferably, the concentration of the epoxyamine in the adhesive is between about 25 percent by weight and about 75 percent by weight, and more preferably, between about 45 percent by weight and about 55 percent by weight.

The adhesive may include curing agents. Curing agents react with the epoxyamine and can accelerate the curing process of the adhesive in which a secure adhesive bond is formed. Curing agents include functional groups reactive with the epoxyamines. Suitable functional groups include, for example, thiol, alcohol, amine and mercapto functional groups. Suitable curing agents include, for example, diethylene triamine, triethylene teramine, thiosulfates, diaminopentanes such as 1,5 diaminopentane, and alcohols such as proylene glycol and glycerol. Suitable curing agents for mercapto functional groups include tertiary amine catalysts, such as tris-dimethyl amino phenol. Curing agents for amine functional groups include, for example, dimethylurea. Lewis acids may also be used as curing agents for the epoxyamine adhesives. Lewis acids can induce cationic polymerization of epoxyamine compounds. Some compounds may accelerate the curing process by functioning as a catalyst rather than forming permanent bonds with the adhesive. Preferred curing agents are non toxic and include, for example, 1,5 dithiopentane and 1,5 diaminopentane. In addition, addition of heat can accelerate the curing with or without the addition of a curing agent.

The concentration of the curing agent in the adhesive, if used, can be between about 1 percent by weight and about 20 percent by weight. Preferably the concentration of the curing agent in the adhesive is between about 3 percent by weight and about 15 percent by weight, more preferably between about 5 percent by weight and about 10 percent by weight. The concentration of the curing agent can be selected, for example, based on the desired cure time of the adhesive. Higher concentrations of the curing agent may decrease the cure time of the adhesive.

The curing agent may also be prepared as a separate composition. The curing agent composition may be contacted with the adhesive composition shortly before formation of the adhesive bond is desired. In some embodiments, contact of the adhesive with the curing agent can greatly accelerate the curing process and may result in curing of the adhesive before the desired elapsed time. In such instances, it may be desirable to associate the adhesive with a first substrate and the curing agent with the second substrate so that the curing can occur rapidly once the two substrates are joined.

The adhesive can, optionally, include flexibilizers. Flexibilizers can be included in the adhesive to provide flexibility to the adhesive bond upon curing. Flexibilizers may be naturally occuring compositions. Suitable flexiblizers include synthetic and natural rubbers, other flexible, synthetic polymers, natural non-native biocompatible proteins, such as exogenous (i.e., non-native) collagen and the like, glycosaminoglycans (GAGs), such as haluronin and chondroitin sulfate, and blood components, such as fibrin, fibrinogen, albumin and other blood factors.

The concentration of the flexibilizers in the adhesive can be. between about 1 percent by weight and about 40 percent by weight. Preferably the concentration of the flexibilizer in the adhesive is between about 10 percent by weight and about 30 percent by weight, more preferably between about 15 percent by weight and about 25 percent by weight. The concentration of the flexibilizers in the adhesive can be selected based on the desired flexibility of the adhesive bond.

The adhesive may also include salts and/or buffers. Suitable salts can include, for example, sodium chloride, potassium chloride and the like. Suitable buffers can include, for example, the following compounds: ammonium, phosphate, borate, bicarbonate, carbonate, cacodylate, citrate, and other organic buffers such as tris(hydroxymethyl) aminomethane (TRIS), morpholine propanesulphonic acid (MOPS), and N-(2-hydroxyethyl) piperazine-N'(2-ethanesulfonic acid) (HEPES). Suitable buffers are generally chosen based on the desired pH range for the adhesive composition. Borate buffers, for example, act as buffers in the pH range of between about 6 and about 8.

The selection of a suitable buffer and/or a suitable salt can depend on the specific use of the adhesive composition. The adhesive composition generally has a faster rate of curing in basic pH. When the adhesive composition is used in a surgical setting, for example, the adhesive composition is generally at a physiological pH and ionic strength. When the adhesive composition is used with non-tissue substrates and/or during manufacturing, for example, the pH of the adhesive composition can be basic.

The adhesives can contain additional additives to modify the mechanical properties of the adhesive. Suitable additives include, for example, fillers, softening agents and stabilizers. Representative fillers include, for example, carbon black and metal oxides, silicates, acrylic resin powder, and various ceramic powders. Representative softening agents include, for example, dibutyl phosphate, dioctylphosphate, tricresylphosphate, tributoxyethyl phosphates and other esters. Representative stabilizers include, for example, trimethyldihydroquinone, phenyl-$\beta$-naphthyl amine, p-isopropoxydiphenylamine, diphenyl-p-phenylene diamine and the like.

D. Association of the Adhesive with the Substrate

The adhesive is generally associated with at least a portion of a first substrate. The adhesive associated with the first substrate can be applied as a coating, bound covalently to the substrate, and/or incorporated into the substrate matrix or structure. The first substrate associated with the adhesive is secured to a second substrate to form an adhesive bond between the first substrate and the second substrate when the adhesive cures.

The adhesive may be associated with the substrate by coating. To associate the adhesive with the substrate by coating, the substrate can be placed in a solution containing the adhesive. Alternatively, the adhesive can be brushed onto the surface, administered from an applicator or sprayed on as an aerosol or the like. The adhesive can be added to the substrate and dried to remove the solvent. Alternatively, the adhesive can be applied as a solution with the resulting composite being kept moist to prevent the substrate/adhesive composite from drying. out. A suitable container for the storage of moisture sensitive substrate/adhesive component composites is described in U.S. Pat. No. 5,960,956, entitled "Storage Container," incorporated herein by reference.

Application of the adhesive as a coating over the selected portion of the substrate is generally sufficient to provide strong association. The strong association of the adhesive coating can be due to natural attractions between the substrate material and the adhesive, covalent bonding with the substrate, natural wetting effects of the adhesive on a surface and/or other similar effects.

In some preferred embodiments, the adhesive is covalently linked with the substrate. Generally, epoxyamine adhesives have functional groups that are active and can bond with functional groups on the substrates. Correspondingly, suitable substrates have functional groups capable of bonding with epoxyamine. If the adhesive is covalently bonded to the substrate, a suitable amount and corresponding thickness of the adhesive is bonded to the substrate to form an adhesive bond while maintaining the adhesive capability of the surface of the adhesive to bond to a second substrate.

The adhesive may be associated with a portion of a substrate or with all of the substrate. In some embodiments, only a portion of the first substrate and a portion of the second substrate may be associated with an adhesive. In other embodiments, the surface of both substrates may be associated with the adhesive.

The adhesive can be associated with the substrate just prior to the forming of the adhesive interface, although the precise timing can be adjusted based on a variety of factors. Relevant timing factors include cure rate, the timing of the surgical procedure, and the stability of the adhesive under the environmental conditions, such as humidity, in which they are applied.

After the adhesive has been applied to the first substrate, the first substrate can be joined to the second substrate. The first substrate can be bound to a second substrate before or during the process of implanting a medical device. For example, this process can be performed at a patient care facility as part of the procedure using the medical device. Thus, the multiple substrates adhered to each other with the adhesive are implanted in a patient prior to, during or after complete curing of the adhesive. When used during the implantation of the medical device, one of the substrates can be the patient's native tissue. The attachment of the substrates to each other using the procedures herein can be advantageous due to localization of the adhesive and generally increased bond strength relative to biological glues.

Since the adhesives can be used to attach substrates of a medical device prior to implantation, the adhesive can be used in a manufacturing context. In a manufacturing context, the administration and curing of the adhesive can be performed under controlled conditions. All or a portion of the manufacturing process can be automated. In some embodiments, the medical devices are not necessarily implantable.

The adhesive composition can include a one part composition. The one part can include the epoxyamine and any other desired components, i.e. curing agent, flexibilizers and the like. Alternatively, the adhesive can include a multiple-part composition. Each part of the composition can include one or more of the components in the adhesive composition such that when all the parts are combined the desired adhesive composition is formed. When the adhesive includes multiple parts, the different parts may all be placed on the same substrate. Alternatively, the different parts of the adhesive composition can be placed on different substrates. When the adhesive includes an epoxyamine and a curing agent, for example, the epoxyamine can be associated with the first substrate and the curing agent with the second substrate. An adhesive bond can then be formed when the first substrate is joined to the second substrate and the adhesive is allowed to cure. Different components of the multiple component adhesive can be mixed prior to application. Alternatively, the components can be mixed during application using a syringe with multiple reservoirs that lead to a common applicator tip. In other embodiments the components are added sequentially.

The adhesive composition can be used in surgical settings. Surgical settings include operating rooms, emergency rooms and the like. The physician, for example, can use the adhesive for implanting a prosthesis, for adhering a patients' native tissue to itself and the like.

The adhesive composition can also be used in manufacturing settings. Manufacturing settings can include settings where medical devices are assembled. Heart valve prostheses, for example, are particularly amenable to manufacturing using the adhesive composition. One or more of the heart valve leaflets can be associated with the support structure by an adhesive to form a heart valve prosthesis. The adhesive may be applied to a supporting structure such as a stent or a conduit that supports a prosthesis. The adhesive may be used, for example, to adhere a sewing cuff to a heart valve prosthesis and/or to native tissue in a patient.

Figure 3:
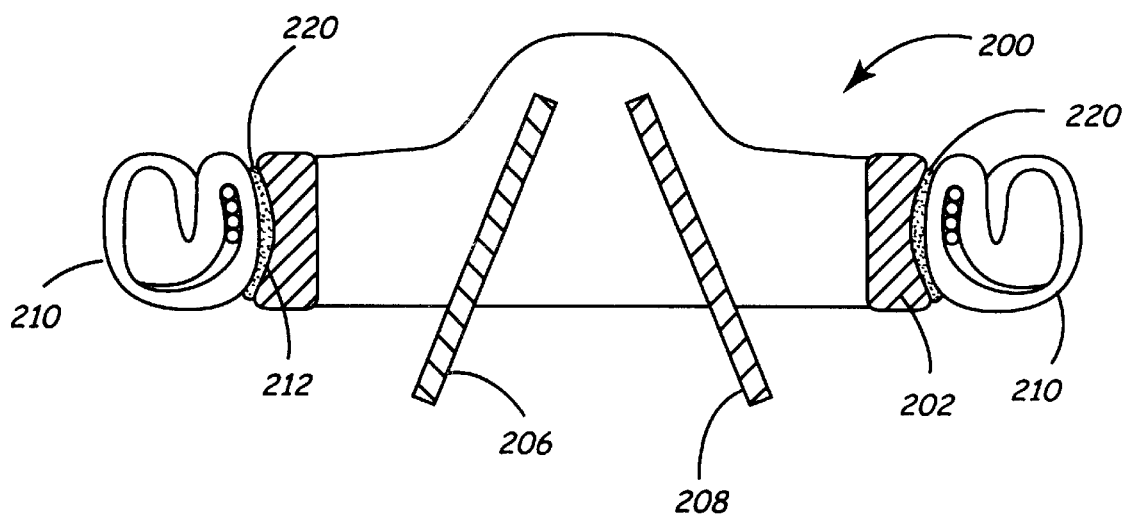
FIG. 3 is a sectional view of a mechanical heart valve prosthesis taken through the center of the valve.

Referring to FIG. 3, the cross section of one embodiment of a heart valve 200 is depicted. Heart valve 200 includes an orifice 202 that forms a blood flow path through the interior of orifice 202. Heart valve 200 is depicted as a bileaflet valve with two leaflets or occluders 206, 208 that pivot between an open position and a closed position such that the blood flow path through orifice 202 is correspondingly open or closed. Sewing cuff 210, which generally can be made of fabric, is located at the exterior 212 of orifice 202 substantially out of the path of blood flow. Sewing cuff 210 can be adhered by adhesive composition 220 to orifice 202.

Preferred adhesives for surgical procedures have cure times ranging from about 1 minute to about 5 hours, more preferably from about 5 minutes to about 1 hour, and even more preferably from about 5 minutes to about 30 minutes. Preferred adhesives for medical device manufacturing have cure times ranging from about 1 minute to about 48 hours, more preferably from about 5 minutes to about 24 hour, and even more preferably from about 5 minutes to about 8 hours.

In some embodiments, a curing agent may be contacted with the adhesive composition when the initiation and/or acceleration of the curing rate is desired. The reaction rate of an adhesive composition can, for example, be increased by about two fold if a nitrogen containing curing agent such as an amine is contacted with or included in the adhesive composition. Similarly, the reaction rate of an adhesive composition can, for example, be increased by about 100 fold if a sulfur containing curing agent such as a thiol is contacted with or included in the adhesive composition. The curing rates would be expected to increase corresponding to the reaction rates, with the cure rates depending, for example, on the concentrations of all of the components.

After the application of the adhesive, the first substrate is contacted with a second substrate at the desired point of attachment. A variety of approaches can be used to hold the first substrate to the second substrate while the adhesive cures sufficiently. The adhesive has cured sufficiently when the adhesive bond can hold against standard stresses applied to the adhesive bond without the need for additional support. Standard stresses can vary over significant ranges. For example, the stresses can be relatively low for adhesives holding a surgical patch or higher for adhesives securing a heart valve prosthesis within the patient. When fully cured, the adhesive bond reaches levels of strength to meet expected durability requirements.

With respect to initial curing of the adhesive, a health care professional or manufacturing personnel can hold or maintain the substrate in place long enough to reach sufficient adhesion. Alternatively, clamps, clips or the like can be used to hold the substrate in place. These approaches can be used with adhesives having reasonably rapid cure rates. Alternatively, or in addition, a few suture stitches or staples can be applied to hold the substrate in place. A suitable degree of suturing or stapling generally would be considerably less using the adhesive than the degree of suturing or stapling required if the suture or staples were providing the primary support for the attachment of the substrate. In some embodiments, the sutures and/or staples may be removed after the adhesive has cured. The limited use of suture and/or staples are intended to provide stabilization to the adhesive bond at the early stages of curing to prevent separation of the adhesive bond.

E. Properties of the Adhesive Bond

After the application of the adhesive, a junction, seal or adhesive bond is formed between the first substrate and the second substrate with at least a portion of the adhesive between the first substrate and the second substrate. The junction may involve a "seamless joining" of the second substrate to the first substrate in the sense of a smooth connection between the two materials.

The adhesive bond includes the overlapping region of the substrates with the adhesive between the first substrate and the second substrate. The adhesive bond preferably has a bond strength of at least about 0.01 $kg/mm^2$ and more preferably at least about 0.05 $kg/mm^2$. Since it is not possible to measure the bond strength of an actual adhesive bond, for embodiments in which a substrate is attached to native tissue in a patient. The bond strength, for these embodiments, can be estimated by reference to a comparable adhesive bond formed between a similar section of substrate and a piece of tissue that is roughly equivalent to the native tissue in the actual adhesive bond.

Figure 4:
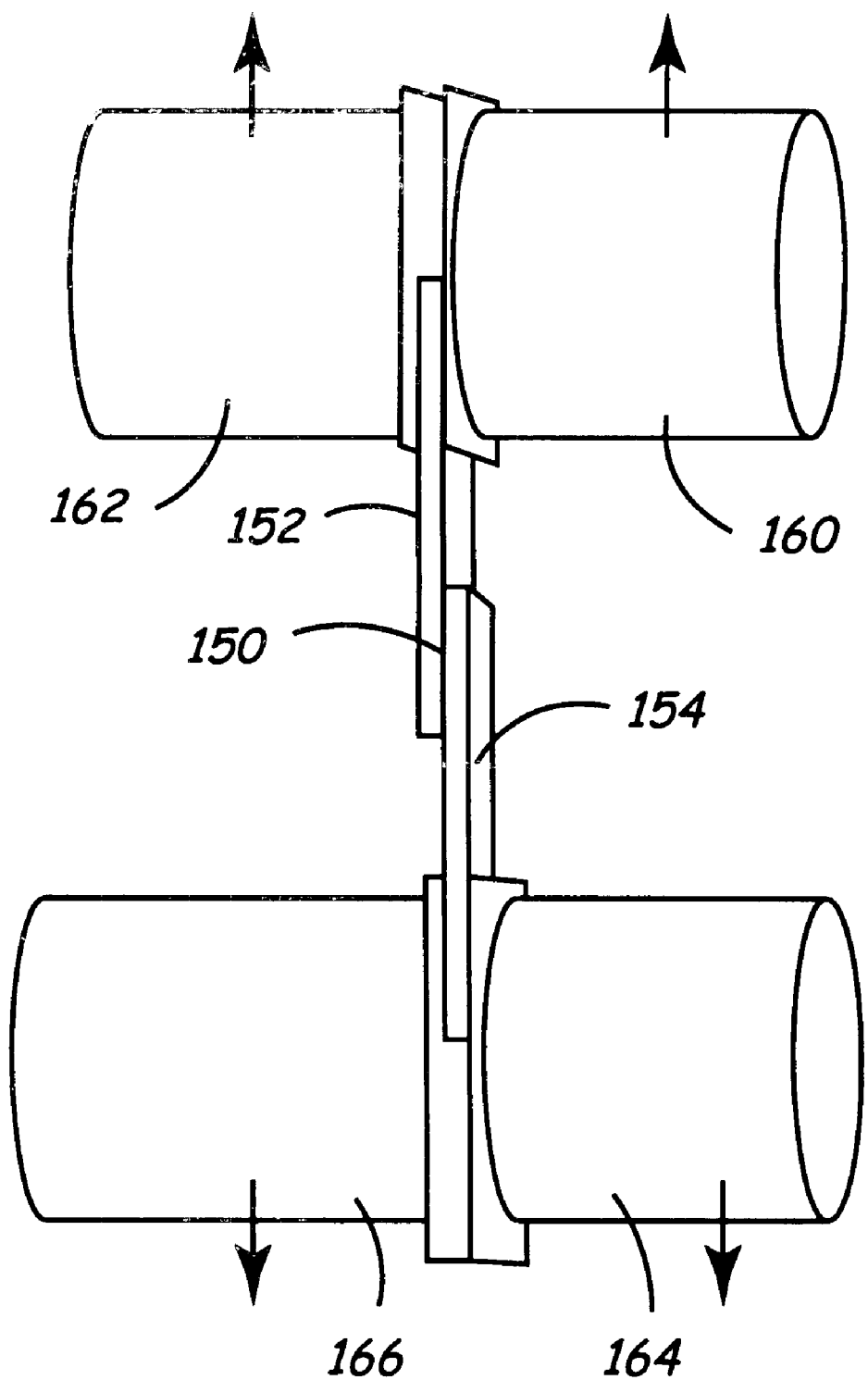
FIG. 4 is a perspective view of a testing apparatus for measuring shear tear strength of an adhesive bond.

Referring to FIG. 4, the bond strength is measured by forming an adhesive bond 150 at overlapping edges of a portion of substrate 152 and a section of fresh tissue 154, i.e., tissue without fixation, such that substrate 152 and tissue 154 extend in opposite directions from the adhesive bond 150. A different substrate can be used instead of the tissue, as appropriate. The edges extending away from the adhesive bond are held between clamps 160, 162, 164, 166.

Adhered substrates 152, 154, positioned between clamps 160, 162, 164, 166, are pulled, as shown in FIG. 4, in the respective direction in which they extend from the adhesive bond 150 until the adhesive bond ruptures under the shear forces. The value of the shear force (tear strength) applied when the adhesive bond breaks divided by the area of the adhesive bond is a measure of the bond strength. While actual adhesive bonds may not be planar, i.e., flat, the bond strengths are evaluated as planar adhesive bonds for consistency. The bond strengths of nonplanar adhesive bonds generally should be roughly equal to the area of the adhesive bond multiplied by the planar bond strength per area if a good hemostatic or liquid tight seal is formed around the adhesive bond.

Parts of the adhesive may be resorbable. The resorbable components in the adhesive are resorbed preferably over a time period during which the substrate and tissue are joined together during natural healing processes. Thus, the adhesive may be replaced by natural tissue without compromising the integrity of the adhesive bond. Variations in the resorption rate can be adjusted empirically to ensure that the resorbable adhesive components remain at least for sufficient periods of time so that the strength of the adhesive bond is not compromised.

F. Biologically Active Additives

The adhesive can also include biological response modifiers. Inclusion of biological response modifiers within the adhesive can result in the gradual release of the biological response modifier, especially if the adhesive is partially resorbable. Suitable biological response modifiers include, for example, antimicrobial agents, anticalcification agents and growth factors. In particular, growth factors can be effective to stimulate growth of native tissue near or at the adhesive bond, which can be especially useful for resorbable adhesives.

Antimicrobial agents include, for example, antibiotic organic chemical agents and antimicrobial metal ions. Organic antibiotic agents include, for example, penicillin and the like. Antimicrobial metal ions include, for example, ions of Ag, Au, Pt, Pd, Ir, Cu, Sn, Sb, Pb, Bi, Zn and combinations thereof. To associate the antimicrobial metal ions with the prosthesis, the prosthesis or a portion of the prosthesis can be soaked in a solution of the antimicrobial metal ions, such as a silver nitrate solution. Alternatively, the solution can be sprayed, brushed or similarly applied to the substrate.

Alternatively, antimicrobial metal ions can be applied in the form of an antimicrobial metal salt with a relatively low solubility in aqueous solutions. Silver compounds are particularly preferred. Suitable silver compounds include, for example, silver chloride, silver bromide, silver iodide, silver carbonate and silver phosphate. Suitable copper compounds include, for example, cupric stearate and cupric phosphate. Suitable zinc compounds include, for example, zinc stearate and zinc phosphate. Similarly, suitable palladium compounds include, for example, palladium acetate.

Certain polyvalent metal ions are effective at reducing calcification of prostheses. Preferred anticalcific metal ions include, for example, aluminum ions ($Al^{+3}$) and ferric ions ($Fe^{+3}$). Other suitable metal ions include, for example, manganese ions, zinc ions, gallium ions, lanthanum ions and beryllium ions. To introduce the polyvalent anticalcific metal ions into the prosthesis, the prosthesis or a portion of the prosthesis can be soaked in a solution of the anticalcific ions. For example, aluminum nitrate or ferric nitrate can be used. Alternatively, the anticalcific metal ions can be deposited as a relatively insoluble salt by the addition of a selected anion to a solution of soluble salt of an anticalcific cation in contact with a prosthesis or a portion of a prosthesis. For example, aluminum palmitate can be precipitated from a solution of aluminum chloride by the addition of palmitic acid, and ferric phosphate can be precipitated from a solution of ferric chloride.

The biological response modifier can be a growth factor. A particularly preferred growth factor includes, for example, vascular endothelial growth factor (VEGF). VEGF encourages the proliferation of endothelial cells which line vascular tissue. VEGF is a protein that can be included within the adhesive composition or attached to one of the substrates. The association of VEGF with prostheses is described further in copending and commonly assigned U.S. patent applications Ser. Nos. 09/014,087 and 09/186,810 to Carlyle et al., both entitled "Prostheses With Associated Growth Factors," both of which are incorporated herein by reference.

Other desirable growth factors include, in particular, transforming growth factor-beta (TGF-beta). TGF-beta has a chemotactic effect on fibroblasts and stimulates fibroblasts to produce an extracellular matrix including collagen. In combination with a TGA adhesive or other adhesives for medical devices, TGF-beta may help attract native/host tissues onto a substrate, such as a heart valve prosthesis, to coat the substrate with host tissue. The substrate coated with host tissue is less likely to be immunogenic. In generally, the adhesive would include a concentration from about 5 picomolar to about 50 nanomolar TGF-beta.

G. Storage, Packaging, Distribution and Use

Following adhesion of substrates in prostheses, the prostheses can be stored. In some embodiments, a substrate associated with the adhesive may also be stored, i.e. prior to forming an adhesive bond. If the substrate with the adhesive is stored prior to completing the adhesive bond, the adhesive generally is associated with the substrate such that large numbers of adhesive molecules are not easily dissociated from the substrate over the period of time required for curing of the adhesives.

Preferably, a coating of the adhesive is stable for some period of time, preferably days or longer under proper storage. Association of the adhesive coating with the substrate can form following at least an hour, and in some cases following two hours or more of contact between the adhesive and the substrate. The substrate with the associated adhesive generally is prepared and stored prior to its intended use.

Preferred storage techniques minimize the risk of microbial contamination. For example, prostheses including substrates that are not moisture sensitive can be stored in a dry air tight container. Alternatively, prostheses can be stored in a sterile sealed container with an antiseptic solution. The nature of the antiseptic solution should be compatible with the substrate and maintain the adhesive bond and/or the activity of the adhesive. For example, a crosslinked tissue substrate with the adhesive can be stored in a dilute aqueous glutaraldehyde solution. Due consideration should be given to possible loss over time of the bonded adhesive or the efficiency of the bonded adhesive. Additives, including antioxidants, such as ascorbic acid, can be added to the storage solution to reduce the loss of efficiency of the adhesive during storage.

For distribution, the prostheses can be placed in sealed and sterile containers. The containers are generally dated such that the date reflects the maximum advisable storage time considering possible degradation of the adhesive component as well as other factors. The containers are packaged along with instructions for the proper use of the prosthesis and along with appropriate and/or required labeling. The containers are distributed to health care professionals for use in appropriate medical procedures. If the medical articles are stored in a solution, a health care professional may rinse the prosthesis after removing it from the storage container just before its use.

Alternatively, a substrate can be associated with the adhesive at the hospital or another site remote from the production facility. The substrate with the adhesive, thus, may only be stored a short period of time prior to use. In this case, the substrate and adhesive needed to modify the substrate can be distributed separately or together. Appropriate instructions can be distributed with either the substrate and/or the adhesive. For short term storage, the modified substrate can be kept in the solution used for modifying the substrate. Alternatively, the modified substrate can be used immediately after completing the adhesion of the different substrates.

EXAMPLES

Example 1

Gelation Times

This example illustrates the gelation times of different TGA formulations.

TGA was obtained from Hawkins Chemical Co. (Minneapolis, Minn.). The TGA was produced following the procedure outlined in FIG. 2 and discussed above. Bovine albumin was purchased from Sigma Chemical Co. D-Methionine was purchased from Aldrich Chemical Co. L-Lysine was purchased from Sigma Chemical Co., and Vitrogen 100 was purchased from Collagen Corporation.

The following aqueous preparations were produced (percentages are by weight):

1. TGA (75%) alone
2. TGA (75%)+albumin (10%)
3. TGA (75%)+vitrogen (5% collagen)
4. TGA (75%)+Lysine (10%)
5. TGA (75%)+Methionine (10%)

Each of the formulations were mixed in 10 ml glass beakers with a glass stir rod until uniform. Observations were recorded at 0, 5 sec., 5 min., 10 min., 20 min., 60 min., 120 min., 450 min., 1080 min. and two days.

Observations were made at each time point, and notable changes are summarized here. Initially, all samples were slightly viscous. At the five second time point, TGA-albumin, TGA-vitrogen, TGA-methionine and TGA-lysine all showed signs of initial thickening, yet TGA alone remained unchanged from the initial state. At five minutes, TGA-albumin and TGA-vitrogen had significantly thickened and were exhibiting signs of adhesion to a glass stirring-rod. Also at five minutes, TGA-methionine and TGA-lysine showed signs of thickening with precipitaton formation. Only incremental changes in increased adhesion were visible in TGA alone at five minutes. At the ten minute time point, TGA-albumin, TGA-vitrogen, TGA-methionine and TGA-lysine all exhibited properties of being firm, flexible and sticky. No further changes were observed in TGA alone at ten minutes. The next notable change occurred at 450 minutes with TGA alone thickening. The final observation at two days showed that TGA, TGA-lysine, and TGA-methionine were all. very hard resin-like materials, yet the TGA-albumin and the TGA-vitrogen were still flexible, plastic-like materials.

Example 2

Adhesive strength of TGA adhesives

This example demonstrates the strength of the adhesive bond of various adhesive formulations. TGA based adhesives were compared with Loctite®, a cyanoacrylate medical adhesive purchased from Loctite U.S.A. Corporation (Rocky Hill, Conn.).

Four different aqueous formulations of adhesives were used, as follows (percentages by weight):

1. TGA (75%)—see above 75% TGA
2. TGA (75%)—Albumin (10%) from above
3. TGA (75%)—Diaminopentane (5%)
4. Positive control—Loctite.

A lap shear test was conducted using these various formulations. The tests were conducted on glutaraldehyde fixed pericardium. Pericardium strips of 1 cm by 5 cm were used. Adhesive was coated onto an area of about 1 square centimeter using a syringe. The strips were overlapped to form a bond and were allowed to cure for about one hour at room temperature.

The strength of the bond was tested on an Instron 50 lb Load Cell, MOdel Sintech 1/S from the Sintech Division of MTS Systems Corporation (Research Triangle Park, N.C.). The full width of the two joined tissue pieces was gripped in the load cell to apply an even force across the adhesive bond. The load that results in sufficient shear force to tear the adhesive bond was measured using the apparatus as shown in FIG. 4.

The results are presented in Table 1. Samples with TGA alone delaminated when handled, possibly due to a cure rate greater than one hour. The samples adhered with TGA alone until they were handled.

TABLE 1

|  | Peak Load (Kg) | Peak Stress (Kg/mm$^2$) | Modulus (Kg/mm$^2$) |
| --- | --- | --- | --- |
| TGA + alb. | | | |
| 1 | 0.25 | 0.27 | 1.47 |
| 2 | 0.44 | 0.48 | 2.02 |
| 3 | 0.89 | 0.97 | 3.85 |
| Mean | 0.53 | 0.57 | 2.45 |
| Std. Dev. | 0.33 | 0.36 | 1.25 |
| TGA + diaminopent. | | | |
| 1 | 0.31 | 0.34 | 2.25 |
| 2 | 0.14 | 0.15 | 1.24 |
| 3 | 0.27 | 0.30 | 1.55 |
| Mean | 0.24 | 0.26 | 1.68 |
| Std. Dev. | 0.09 | 0.10 | 0.52 |
| Loctite ™ | | | |
| 1 | 0.85 | 0.92 | 3.39 |
| 2 | 1.79 | 1.95 | 4.85 |
| 3 | 1.33 | 1.44 | 4.04 |
| Mean | 1.32 | 1.44 | 4.09 |
| Std. Dev. | 0.47 | 0.51 | 0.73 |

The synthetic cyanoacrylate (Loctite™) provided the strongest bonding, yet may be limited in use in medical products due to its tissue toxicity. The other TGA-based adhesives also formed strong bonds. TGA with albumin provided stronger bond strength than the TGA with diaminopentane. This demonstrates that the TGA-based adhesives are suitable for tissue adhesives and as adhesives generally for medical devices.

The embodiments above are intended to be illustrative and not limiting. Additional embodiments are within the claims. Although the present invention has been described with reference to preferred embodiments, workers skilled in the art will recognize that changes may be made in form and detail without departing from the spirit and scope of the invention.

What is claimed is:

1. An adhesive composition comprising an epoxyamine and a curing agent, wherein the epoxyamine is at a concentration of between about 25 percent by weight and about 90 percent by weight, wherein the adhesive composition is biocompatible.

2. The adhesive composition of claim 1 wherein an adhesive bond is formed when the adhesive composition is associated with a first substrate and joined to a second substrate.

3. The adhesive composition of claim 1 wherein the epoxyamine is triglycidyl amine.

4. The adhesive composition of claim 1 wherein the curing agent comprises a functional group selected from the group consisting of sulfur-containing functional groups, nitrogen-containing functional groups and oxygen-containing functional groups.

5. The adhesive composition of claim 1 wherein the curing agent comprises a functional group selected from the group consisting of a thiol, an alcohol and an amine.

6. The adhesive composition of claim 1 wherein the adhesive composition further comprises a flexibilizer.

7. The adhesive composition of claim 6 wherein the flexibilizer is selected from the group consisting of collagen, albumin, glycosaminoglycans and combinations thereof.

8. The adhesive composition of claim 2 wherein the adhesive bond is formed after at least about one minute.

9. The adhesive composition of claim 1 wherein the curing agent is between about 1 percent by weight and about 20 percent by weight of the adhesive composition.

10. The adhesive composition of claim 6 wherein the flexibilizer is between about 1 percent by weight and about 40 percent by weight of the adhesive composition.

11. The adhesive composition of claim 1 further comprising a biological response modifier.

12. The adhesive composition of claim 11 wherein the biological response modifier comprises transforming growth factor-beta.

13. A medical adhesive comprising an adhesive composition and transforming growth factor-beta wherein the adhesive composition comprises an epoxyamine.

14. A medical device having two substrates secured with a cured form of the adhesive of claim 13.

15. The medical device of claim 14 wherein the medical device is an implantable prosthesis.

16. The adhesive composition of claim 1, wherein the epoxyamine comprises a plurality of different epoxyamine compounds.

17. The adhesive composition of claim 1, wherein the composition further comprises a resorbable composition.

18. The adhesive composition of claim 1, wherein the adhesive composition further comprises a solvent.

19. The adhesive composition of claim 18, wherein the solvent comprises water.

20. The adhesive composition of claim 19, wherein the solvent further comprises a buffer.

21. The adhesive composition of claim 19, wherein the adhesive composition further comprises salt.

22. The adhesive composition of claim 1, wherein the adhesive composition further comprises a softening agent.

23. The adhesive composition of claim 11, wherein the biological response modifier comprises an antimicrobial agent.

24. The adhesive composition of claim 11, wherein the biological response modifier comprises an anticalcification agent.

25. The adhesive composition of claim 2, wherein the fist substrate and the second substrate are native tissue.

26. A prosthesis, wherein the prosthesis comprises a first substrate and a second substrate, wherein the first substrate and the second substrate are adhered by the adhesive composition of claim 1.

27. The medical adhesive of claim 13, wherein the adhesive composition further comprises a curing agent.

28. The medical adhesive of claim 27, wherein the curing agent is between about 1 percent by weight and about 20 percent by weight of the adhesive composition.

29. The medical adhesive of claim 13, wherein the epoxyamine comprises triglycidylamine.

* * * * *